(12) United States Patent
Güiraldes et al.

(10) Patent No.: US 12,279,573 B2
(45) Date of Patent: Apr. 22, 2025

(54) WHEAT VARIETY '10020777675'

(71) Applicant: GDM SEEDS INC., Gibson City, IL (US)

(72) Inventors: Marcos Quiroga Güiraldes, Gibson City, IL (US); Juan Ignacio Severo, Gibson City, IL (US)

(73) Assignee: GDM Seeds Inc., Gibson City, IL (US)

( * ) Notice: Subject to any disclaimer, the term of this patent is extended or adjusted under 35 U.S.C. 154(b) by 243 days.

(21) Appl. No.: 17/592,854

(22) Filed: Feb. 4, 2022

(65) Prior Publication Data

US 2022/0240471 A1 Aug. 4, 2022

Related U.S. Application Data

(60) Provisional application No. 63/145,836, filed on Feb. 4, 2021.

(51) Int. Cl.
*A01H 5/10* (2018.01)
*A01H 6/46* (2018.01)

(52) U.S. Cl.
CPC ............. *A01H 6/4678* (2018.05); *A01H 5/10* (2013.01)

(58) Field of Classification Search
None
See application file for complete search history.

(56) References Cited

U.S. PATENT DOCUMENTS 10,271,499 B1 * 4/2019 Gray .................. C12N 15/8279

* cited by examiner

*Primary Examiner* — Cynthia E Collins
(74) *Attorney, Agent, or Firm* — Morrison & Foerster LLP

(57) ABSTRACT

New wheat variety designated '10020777675' is described. '10020777675' is a wheat variety exhibiting stability and uniformity.

15 Claims, No Drawings

WHEAT VARIETY '10020777675'

CROSS-REFERENCE TO RELATED APPLICATIONS

This application claims the benefit of U.S. Provisional Application No. 63/145,836, filed Feb. 4, 2021, the contents of which are hereby incorporated by reference in their entirety.

FIELD OF THE INVENTION

The present invention relates to the field of plant breeding. In particular, this invention relates to new wheat, *Triticum aestivum* L., varieties designated '10020777675', '10020777765', and '20646295'.

BACKGROUND OF THE INVENTION

Wheat is one of the oldest and most widely cultivated grain crops. Common wheat (*Triticum aestivum* L.) is a hexaploid species that may be classified into five different market classes: common wheat, hard red winter, hard red spring, soft red winter, and white. Durum wheat (*Triticum turgidum* L.) is a tetraploid species, which makes up a sixth market class. Additional less widely cultivated wheat species include hexaploid spelt (*Triticum spelta*), tetraploid emmer (*Triticum dicoccon*), and diploid einkorn (*Triticum monococcum*). The wheat grain is a staple food worldwide for animals and humans. Commodity plant products produced from the wheat grain include protein concentrate, protein isolate, hulls, meal, flour, oil and the whole wheat grain itself. Wheat grains and other plant parts may also be used to produce a variety of other products, including, but not limited to, baked goods, cereals, crackers, pasta, beverages, livestock feed, biofuel, straw, construction materials, and starches. Due to the nature of plant science agriculture, broadly defined as a manipulation of available plant resources to meet the needs of the growing human population, the environment in which plants are grown for agricultural production continuously offers new obstacles to agricultural production. Each new cultivar released to agricultural production is selected for the purpose of increasing yield resulting from increased disease resistance to prevalent diseases, or from direct or indirect improvement in yield potential or efficiency of production. Development of stable, high yielding cultivars with superior characteristics is an ongoing goal of wheat breeders.

Accordingly, there is a continuing need to develop new wheat varieties that are stable, high yielding cultivars, and express superior agronomic characteristics.

SUMMARY OF THE INVENTION

In order to meet these needs, the present invention is directed to improved wheat varieties.

In one embodiment, the present invention is directed to a wheat seed designated as '10020777675' having ATCC Accession Number PTA-127799. In one embodiment, the present invention is directed to a wheat plant and parts isolated therefrom produced by growing '10020777675' wheat seed. In another embodiment, the present invention is directed to a wheat plant and parts isolated therefrom having all the physiological and morphological characteristics of a wheat plant produced by growing '10020777675' wheat seed having ATCC Accession Number PTA-127799. In still another embodiment, the present invention is directed to an F1 hybrid wheat seed, plants grown from the seed, a pollen grain, an ovule, a protoplast, a cell, an embryo, a cotyledon, a hypocotyl, a meristem, a root, a head, a shoot, a glume, an awn, a pericarp, an endosperm, a pistil, an anther, a flower, a stem, a leaf, a petiole, or a portion thereof, isolated therefrom having '10020777675' as a parent, wherein '10020777675' is grown from '10020777675' wheat seed having ATCC Accession Number PTA-127799.

Wheat plant parts include seed, a pollen grain, an ovule, a protoplast, a cell, an embryo, a cotyledon, a hypocotyl, a meristem, a root, a head, a shoot, a glume, an awn, a pericarp, an endosperm, a pistil, an anther, a flower, a stem, a leaf, a petiole, and the like. In another embodiment, the present invention is further directed to a wheat pollen grain, ovule, protoplast, cell, embryo, cotyledon, hypocotyl, meristem, root, head, shoot, glume, awn, pericarp, endosperm, pistil, anther, flower, stem, leaf, and/or petiole isolated from '10020777675' wheat plants. In another embodiment, the present invention is further directed to tissue culture or cells derived from '10020777675' wheat plants.

In still another embodiment, the present invention is further directed to packaging material containing '10020777675' plant parts. Such packaging material includes but is not limited to boxes, paper packaging, plastic packaging, food-grade packaging, etc. The '10020777675' plant parts may be combined with other plant parts of other plant varieties.

In yet another embodiment, the present invention is further directed to a method of selecting wheat plants including (a) growing '10020777675' wheat plants wherein the '10020777675' plants are grown from wheat seed having ATCC Accession Number PTA-127799 and (b) selecting a plant from step (a). In another embodiment, the present invention is further directed to wheat plants, plant parts and seeds produced by the wheat plants wherein the wheat plants are isolated by the selection method of the invention.

In another embodiment, the present invention is further directed to a method of breeding wheat plants including crossing a wheat plant with a plant grown from '10020777675' wheat seed having ATCC Accession Number PTA-127799. In still another embodiment, the present invention is further directed to wheat plants, wheat parts from the wheat plants, and seeds produced therefrom where the wheat plant is isolated by the breeding method of the invention.

In another embodiment, the present invention is directed to methods for producing a wheat plant containing in its genetic material one or more transgenes and to the transgenic wheat plant produced by those methods.

In another embodiment, the present invention is directed to methods for producing a male sterile wheat plant by introducing a nucleic acid molecule that confers male sterility into a wheat plant produced by growing '10020777675' wheat seed, and to male sterile wheat plants produced by such methods.

In another embodiment, the present invention is directed to methods of producing an herbicide resistant wheat plant by introducing a gene conferring herbicide resistance into a wheat plant produced by growing '10020777675' wheat seed, where the gene confers resistantance to a herbicide selected from chlorotoluron, fenoxaprop-p-ethyl, clodinafop, aryloxyphenoxypropionate, diclofop, lauric acid, chlorsulfuron, sulfomethuron, imazanox, quizalofop-p-ethyl, sulfosulfuron, propoxy-carbazone, pyroxsulam, glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant wheat plants produced by such methods.

In yet another aspect, the present invention provides a tissue culture of protoplasts and regenerable cells from a plant or parts thereof, produced by growing seed designated '10020777675', and a wheat plant regenerated from tissue culture.

In yet another aspect, a method of producing a commodity plant product is provided, which includes obtaining a plant grown from '10020777675' wheat seed having ATCC Accession Number PTA-127799, or a part thereof, and producing the commodity plant product therefrom. In some embodiments, the commodity plant product is grain, wheat flour, wheat whole-grain flour, wheat germ flour, wheat brown flour, wheat meal, protein concentrate, baked goods, cereals, pasta, beverages, livestock feed, wheat oil, wheat hulls, biofuel, straw, starches, or construction materials.

In another embodiment, the present invention is directed to methods of producing a pest or insect resistant wheat plan by introducing a gene conferring pest or insect resistance into a wheat plant produced by growing '10020777675' wheat seed, and to pest or insect resistant wheat plants produced by such methods.

In another embodiment, the present invention is directed to methods of producing a disease resistant wheat plant by introducing a gene conferring disease resistance into a wheat plant produced by growing '10020777675' wheat seed, and to disease resistant wheat plants produced by such methods.

In another embodiment, the present invention is directed to methods of producing a wheat plant with a value-added trait by introducing a gene conferring a value-added trait into a wheat plant produced by growing '10020777675' wheat seed, where the gene encodes a protein selected from a ferritin, a nitrate reductase, and a monellin. Certain embodiments are also directed to wheat plants having a value-added trait produced by such methods.

In another embodiment, the present invention is directed to methods of introducing a desired trait into wheat variety '10020777675', by: (a) crossing a '10020777675' plant, where a sample of '10020777675' wheat seed was deposited under ATCC Accession Number PTA-127799, with a plant of another wheat variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a '10020777675' plant to produce backcross progeny plants; (d) selecting for backcross progeny plants that have the desired trait and all of the physiological and morphological characteristics of wheat variety '10020777675'; and (e) repeating steps (c) and (d) two or more times in succession to produce selected third or higher backcross progeny plants that include the desired trait. Certain embodiments are also directed to wheat plants produced by such methods, where the plants have the desired trait and all of the physiological and morphological characteristics of wheat variety '10020777675'. In certain embodiments, the desired trait is herbicide resistance and the resistance is conferred to an herbicide selected from chlorotoluron, fenoxaprop-p-ethyl, clodinafop, aryloxyphenoxypropionate, diclofop, lauric acid, chlorsulfuron, sulfomethuron, imazanox, quizalofop-p-ethyl, sulfosulfuron, propoxycarbazone, pyroxsulam, glyphosate, sulfonylurea, imidazolinone, dicamba, glufosinate, phenoxy proprionic acid, L-phosphinothricin, cyclohexone, cyclohexanedione, triazine, and benzonitrile. In other embodiments, the desired trait is insect or pest resistance and the insect or pest resistance is conferred by a transgene encoding a *Bacillus thuringiensis* endotoxin.

In another embodiment, the present invention provides for single gene converted plants of '10020777675'. The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring wheat gene or a transgene introduced through genetic engineering techniques.

In one embodiment, the present invention is directed to a wheat seed designated as '10020777765'. In one embodiment, the present invention is directed to a wheat plant and parts isolated therefrom produced by growing '10020777765' wheat seed. In another embodiment, the present invention is directed to a wheat plant and parts isolated therefrom having all the physiological and morphological characteristics of a wheat plant produced by growing '10020777765' wheat seed. In still another embodiment, the present invention is directed to an $F_1$ hybrid wheat seed, plants grown from the seed, a pollen grain, an ovule, a protoplast, a cell, an embryo, a cotyledon, a hypocotyl, a meristem, a root, a head, a shoot, a glume, an awn, a pericarp, an endosperm, a pistil, an anther, a flower, a stem, a leaf, a petiole, or a portion thereof, isolated therefrom having '10020777765' as a parent, wherein '10020777765' is grown from '10020777765' wheat seed.

Wheat plant parts include seed, a pollen grain, an ovule, a protoplast, a cell, an embryo, a cotyledon, a hypocotyl, a meristem, a root, a head, a shoot, a glume, an awn, a pericarp, an endosperm a pistil, an anther, a flower, a stem, a leaf, a petiole, and the like. In another embodiment, the present invention is further directed to a wheat pollen grain, ovule, protoplast, cell, embryo, cotyledon, hypocotyl, meristem, root, head, shoot, glume, awn, pericarp, endosperm, pistil, anther, flower, stem, leaf, and/or petiole isolated from '10020777765' wheat plants. In another embodiment, the present invention is further directed to tissue culture or cells derived from '10020777765' wheat plants.

In still another embodiment, the present invention is further directed to packaging material containing '10020777765' plant parts. Such packaging material includes but is not limited to boxes, paper packaging, plastic packaging, food-grade packaging, etc. The '10020777765' plant parts may be combined with other plant parts of other plant varieties.

In yet another embodiment, the present invention is further directed to a method of selecting wheat plants including (a) growing '10020777765' wheat plants wherein the '10020777765' plants are grown from wheat seed and (b) selecting a plant from step (a). In another embodiment, the present invention is further directed to wheat plants, plant parts and seeds produced by the wheat plants wherein the wheat plants are isolated by the selection method of the invention.

In another embodiment, the present invention is further directed to a method of breeding wheat plants including crossing a wheat plant with a plant grown from '10020777765' wheat seed. In still another embodiment, the present invention is further directed to wheat plants, wheat parts from the wheat plants, and seeds produced therefrom where the wheat plant is isolated by the breeding method of the invention.

In another embodiment, the present invention is directed to methods for producing a wheat plant containing in its genetic material one or more transgenes and to the transgenic wheat plant produced by those methods.

In another embodiment, the present invention is directed to methods for producing a male sterile wheat plant by introducing a nucleic acid molecule that confers male sterility into a wheat plant produced by growing '10020777765' wheat seed, and to male sterile wheat plants produced by such methods.

In another embodiment, the present invention is directed to methods of producing an herbicide resistant wheat plant by introducing a gene conferring herbicide resistance into a wheat plant produced by growing '10020777765' wheat seed, where the gene confers resistantance to a herbicide selected from chlorotoluron, fenoxaprop-p-ethyl, clodinafop, aryloxyphenoxypropionate, diclofop, lauric acid, chlorsulfuron, sulfomethuron, imazanox, quizalofop-p-ethyl, sulfosulfuron, propoxy-carbazone, pyroxsulam, glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant wheat plants produced by such methods.

In yet another aspect, the present invention provides a tissue culture of protoplasts and regenerable cells from a plant or parts thereof, produced by growing seed designated '10020777765', and a wheat plant regenerated from tissue culture.

In yet another aspect, a method of producing a commodity plant product is provided, which includes obtaining a plant grown from '10020777765' wheat seed, or a part thereof, and producing the commodity plant product therefrom. In some embodiments, the commodity plant product is grain, wheat flour, wheat whole-grain flour, wheat germ flour, wheat brown flour, wheat meal, protein concentrate, baked goods, cereals, pasta, beverages, livestock feed, wheat oil, wheat hulls, biofuel, straw, starches, or construction materials.

In another embodiment, the present invention is directed to methods of producing a pest or insect resistant wheat plan by introducing a gene conferring pest or insect resistance into a wheat plant produced by growing '10020777765' wheat seed, and to pest or insect resistant wheat plants produced by such methods.

In another embodiment, the present invention is directed to methods of producing a disease resistant wheat plant by introducing a gene conferring disease resistance into a wheat plant produced by growing '10020777765' wheat seed, and to disease resistant wheat plants produced by such methods.

In another embodiment, the present invention is directed to methods of producing a wheat plant with a value-added trait by introducing a gene conferring a value-added trait into a wheat plant produced by growing '10020777765' wheat seed, where the gene encodes a protein selected from a ferritin, a nitrate reductase, and a monellin. Certain embodiments are also directed to wheat plants having a value-added trait produced by such methods.

In another embodiment, the present invention is directed to methods of introducing a desired trait into wheat variety '10020777765', by: (a) crossing a '10020777765' plant, with a plant of another wheat variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a '10020777765' plant to produce backcross progeny plants; (d) selecting for backcross progeny plants that have the desired trait and all of the physiological and morphological characteristics of wheat variety '10020777765'; and (e) repeating steps (c) and (d) two or more times in succession to produce selected third or higher backcross progeny plants that include the desired trait. Certain embodiments are also directed to wheat plants produced by such methods, where the plants have the desired trait and all of the physiological and morphological characteristics of wheat variety '10020777765'. In certain embodiments, the desired trait is herbicide resistance and the resistance is conferred to an herbicide selected from chlorotoluron, fenoxaprop-p-ethyl, clodinafop, aryloxyphenoxypropionate, diclofop, lauric acid, chlorsulfuron, sulfomethuron, imazanox, quizalofop-p-ethyl, sulfosulfuron, propoxy-carbazone, pyroxsulam, glyphosate, sulfonylurea, imidazolinone, dicamba, glufosinate, phenoxy proprionic acid, L-phosphinothricin, cyclohexone, cyclohexanedione, triazine, and benzonitrile. In other embodiments, the desired trait is insect or pest resistance and the insect or pest resistance is conferred by a transgene encoding a *Bacillus thuringiensis* endotoxin.

In another embodiment, the present invention provides for single gene converted plants of '10020777765'. The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring wheat gene or a transgene introduced through genetic engineering techniques.

In one embodiment, the present invention is directed to a wheat seed designated as '20646295'. In one embodiment, the present invention is directed to a wheat plant and parts isolated therefrom produced by growing '20646295' wheat seed. In another embodiment, the present invention is directed to a wheat plant and parts isolated therefrom having all the physiological and morphological characteristics of a wheat plant produced by growing '20646295' wheat seed. In still another embodiment, the present invention is directed to an $F_1$ hybrid wheat seed, plants grown from the seed, a pollen grain, an ovule, a protoplast, a cell, an embryo, a cotyledon, a hypocotyl, a meristem, a root, a head, a shoot, a glume, an awn, a pericarp, an endosperm, a pistil, an anther, a flower, a stem, a leaf, a petiole, or a portion thereof, isolated therefrom having '20646295' as a parent, wherein '20646295' is grown from '20646295' wheat seed.

Wheat plant parts include seed, a pollen grain, an ovule, a protoplast, a cell, an embryo, a cotyledon, a hypocotyl, a meristem, a root, a head, a shoot, a glume, an awn, a pericarp, an endosperm, a pistil, an anther, a flower, a stem, a leaf, a petiole, and the like. In another embodiment, the present invention is further directed to a wheat pollen grain, ovule, protoplast, cell, embryo, cotyledon, hypocotyl, meristem, root, head, shoot, glume, awn, pericarp, endosperm, pistil, anther, flower, stem, leaf, and/or petiole isolated from '20646295' wheat plants. In another embodiment, the present invention is further directed to tissue culture or cells derived from '20646295' wheat plants.

In still another embodiment, the present invention is further directed to packaging material containing '20646295' plant parts. Such packaging material includes but is not limited to boxes, paper packaging, plastic packaging, food-grade packaging, etc. The '20646295' plant parts may be combined with other plant parts of other plant varieties.

In yet another embodiment, the present invention is further directed to a method of selecting wheat plants including (a) growing '20646295' wheat plants wherein the '20646295' plants are grown from wheat seed and (b) selecting a plant from step (a). In another embodiment, the present invention is further directed to wheat plants, plant parts and seeds produced by the wheat plants wherein the wheat plants are isolated by the selection method of the invention.

In another embodiment, the present invention is further directed to a method of breeding wheat plants including crossing a wheat plant with a plant grown from '20646295' wheat seed. In still another embodiment, the present invention is further directed to wheat plants, wheat parts from the wheat plants, and seeds produced therefrom where the wheat plant is isolated by the breeding method of the invention.

In another embodiment, the present invention is directed to methods for producing a wheat plant containing in its genetic material one or more transgenes and to the transgenic wheat plant produced by those methods.

In another embodiment, the present invention is directed to methods for producing a male sterile wheat plant by introducing a nucleic acid molecule that confers male sterility into a wheat plant produced by growing '20646295' wheat seed, and to male sterile wheat plants produced by such methods.

In another embodiment, the present invention is directed to methods of producing an herbicide resistant wheat plant by introducing a gene conferring herbicide resistance into a wheat plant produced by growing '20646295' wheat seed, where the gene confers resistantance to a herbicide selected from chlorotoluron, fenoxaprop-p-ethyl, clodinafop, aryloxyphenoxypropionate, diclofop, lauric acid, chlorsulfuron, sulfomethuron, imazanox, quizalofop-p-ethyl, sulfosulfuron, propoxy-carbazone, pyroxsulam, glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant wheat plants produced by such methods.

In yet another aspect, the present invention provides a tissue culture of protoplasts and regenerable cells from a plant or parts thereof, produced by growing seed designated '20646295', and a wheat plant regenerated from tissue culture.

In yet another aspect, a method of producing a commodity plant product is provided, which includes obtaining a plant grown from '20646295' wheat seed, or a part thereof, and producing the commodity plant product therefrom. In some embodiments, the commodity plant product is grain, wheat flour, wheat whole-grain flour, wheat germ flour, wheat brown flour, wheat meal, protein concentrate, baked goods, cereals, pasta, beverages, livestock feed, wheat oil, wheat hulls, biofuel, straw, starches, or construction materials.

In another embodiment, the present invention is directed to methods of producing a pest or insect resistant wheat plan by introducing a gene conferring pest or insect resistance into a wheat plant produced by growing '20646295' wheat seed, and to pest or insect resistant wheat plants produced by such methods.

In another embodiment, the present invention is directed to methods of producing a disease resistant wheat plant by introducing a gene conferring disease resistance into a wheat plant produced by growing '20646295' wheat seed, and to disease resistant wheat plants produced by such methods.

In another embodiment, the present invention is directed to methods of producing a wheat plant with a value-added trait by introducing a gene conferring a value-added trait into a wheat plant produced by growing '20646295' wheat seed, where the gene encodes a protein selected from a ferritin, a nitrate reductase, and a monellin. Certain embodiments are also directed to wheat plants having a value-added trait produced by such methods.

In another embodiment, the present invention is directed to methods of introducing a desired trait into wheat variety '20646295', by: (a) crossing a '20646295' plant with a plant of another wheat variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a '20646295' plant to produce backcross progeny plants; (d) selecting for backcross progeny plants that have the desired trait and all of the physiological and morphological characteristics of wheat variety '20646295'; and (e) repeating steps (c) and (d) two or more times in succession to produce selected third or higher backcross progeny plants that include the desired trait. Certain embodiments are also directed to wheat plants produced by such methods, where the plants have the desired trait and all of the physiological and morphological characteristics of wheat variety '20646295'. In certain embodiments, the desired trait is herbicide resistance and the resistance is conferred to an herbicide selected from chlorotoluron, fenoxaprop-p-ethyl, clodinafop, aryloxyphenoxypropionate, diclofop, lauric acid, chlorsulfuron, sulfomethuron, imazanox, quizalofop-p-ethyl, sulfosulfuron, propoxycarbazone, pyroxsulam glyphosate, sulfonylurea, imidazolinone, dicamba, glufosinate, phenoxy proprionic acid, L-phosphinothricin, cyclohexone, cyclohexanedione, triazine, and benzonitrile. In other embodiments, the desired trait is insect or pest resistance and the insect or pest resistance is conferred by a transgene encoding a *Bacillus thuringiensis* endotoxin.

In another embodiment, the present invention provides for single gene converted plants of '20646295'. The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring wheat gene or a transgene introduced through genetic engineering techniques.

DETAILED DESCRIPTION OF THE INVENTION

There are numerous steps in the development of novel, desirable wheat germplasm. Plant breeding begins with the analysis of problems and weaknesses of current wheat germplasms, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include increased head size and weight, higher seed yield, improved color, resistance to diseases and insects, tolerance to drought and heat, and better agronomic quality.

Choice of breeding or selection methods can depend on the mode of plant reproduction, the heritability of the trait(s) being improved, and the type of variety used commercially (e.g., F1 hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the case of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, and can include gain from selection per year based on comparisons to an appropriate standard, the overall value of the advanced breeding lines, and the number of successful varieties produced per unit of input (e.g., per year, per dollar expended, etc.).

Promising advanced breeding lines may be thoroughly tested and compared to appropriate standards in environments representative of the commercial target area(s) for at least three years. The best lines can then be candidates for new commercial varieties. Those still deficient in a few traits may be used as parents to produce new populations for further selection. These processes, which lead to the final step of marketing and distribution, may take from ten to twenty years from the time the first cross or selection is made.

One goal of wheat plant breeding is to develop new, unique, and genetically superior wheat varieties. A breeder can initially select and cross two or more parental lines, followed by repeated selfing and selection, producing many new genetic combinations. Moreover, a breeder can generate multiple different genetic combinations by crossing, selfing, and mutations. A plant breeder can then select which germplasms to advance to the next generation. These germplasms may then be grown under different geographical, climatic, and soil conditions, and further selections can be made during, and at the end of, the growing season.

The development of commercial wheat varieties thus requires the development of parental wheat varieties, the crossing of these varieties, and the evaluation of the crosses. Pedigree breeding and recurrent selection breeding methods may be used to develop varieties from breeding populations. Breeding programs can be used to combine desirable traits from two or more varieties or various broad-based sources into breeding pools from which new varieties are developed by selfing and selection of desired phenotypes. The new varieties are crossed with other varieties and the hybrids from these crosses are evaluated to determine which have commercial potential.

Pedigree breeding is generally used for the improvement of self-pollinating crops or inbred lines of cross-pollinating crops. Two parents which possess favorable, complementary traits are crossed to produce an F1. An F2 population is produced by selfing one or several F1's or by intercrossing two F1's (sib mating). Selection of the best individuals is usually begun in the F2 population. Then, beginning in the F3, the best individuals in the best families are selected. Replicated testing of families, or hybrid combinations involving individuals of these families, often follows in the F4 generation to improve the effectiveness of selection for traits with low heritability. At an advanced stage of inbreeding (i.e., F6 and F7), the best lines or mixtures of phenotypically similar lines are tested for potential release as new varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines with each generation due to failure of some seeds to germinate or some plants to produce at least one seed. As a result, not all of the F2 plants originally sampled in the population will be represented by a progeny when generation advance is completed.

In addition to phenotypic observations, the genotype of a plant can also be examined. There are many laboratory-based techniques known in the art that are available for the analysis, comparison and characterization of plant genotype. Such techniques include, without limitation, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs, which are also referred to as Microsatellites), and Single Nucleotide Polymorphisms (SNPs).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding may also be used to introduce new traits into wheat varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in Principles of Cultivar Development by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., Theor. Appl. Genet., 77:889-892 (1989).

Additional non-limiting examples of breeding methods that may be used include, without limitation, those found in Allard, "Principles of plant breeding," John Wiley & Sons, NY, University of California, Davis, Calif., 50-98, 1960; Simmonds, "Principles of crop improvement," Longman, Inc., NY, 369-399, 1979; Sneep and Hendriksen, "Plant breeding perspectives," Wageningen (ed), Center for Agricultural Publishing and Documentation, 1979; Fehr, "Principles of cultivar development," Theory and Technique (Vol 1) and Crop Species Wheat (Vol 2), Iowa State Univ., Macmillan Pub. Co., NY, 360-376, 1987; Poehlman and Sleper, "Breeding Field Crops" Iowa State University Press, Ames, 1995; and Sprague and Dudley, eds., Corn and Improvement, 5th ed., 2006.

Definitions

In the claims, descriptions, and tables that follow, numerous terms are used and are defined as follows:

Awn: The elongated needle-like appendages on the flower- and seed-bearing head at the top of the wheat plant. Awns are attached to the lemmas, which enclose the stamen and the stigma as part of the florets. Florets are grouped in spikelets, which in turn together comprise the head.

Head: As used herein, the term head refers to a group of spikelets at the top of one plant stem. The term spike also refers to the head of a plant located at the top of one plant stem.

Plant maturity: The stage of wheat plant growth at which the development of the seeds, also known as kernels, is complete.

Plant height: Defined as the average height in inches or centimeters of a group of plants, as measured from the ground level to the tip of the head, excluding awns.

Plant growth habit: Refers to the angle formed by the outer leaves of a plant and the tillers when examined visually in an imaginary vertical axis.

Vernalization: The need of vernalization, also referred to as the plant seasonal type, is indicative of the induction of the flowering process of a plant. Winter type plants have high need of vernalization, while spring type plants have no to very weak need of vernalization. Certain plants are alternative types and have a partial need of vernalization.

Overview of the Variety '10020777675'

Wheat variety '10020777675' is a spring-type wheat plant with semi-short yellow heads and awned spikelets.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '10020777675'.

Objective Description of the Variety '10020777675'

The cultivar description information (Table 1) provides a summary of wheat cultivar '10020777675' plant characteristics. Those of skill in the art will recognize that these are typical values that may vary due to environment and that other values that are substantially equivalent are within the scope of the invention. As used herein, "a wheat plant having the physiological and morphological characteristics of wheat cultivar '10020777675'" is a plant having the characteristics set forth in Table 1 when grown in the same environmental conditions.

TABLE 1

| Characteristic | Value |
|---|---|
| Plant | |
| Vernalization | Spring |
| Coleoptile color | White |
| Coleoptile anthocyanin | Absent |
| Juvenile plant growth habit | Semi-erect |
| Color at boot stage | Gray green |
| Height (cm) | 90 |
| Tillering | Sparse (1 to 3) |
| Stem | |
| Waxy bloom | Present |
| Number of nodes at internode | 4 |
| Internode type | Hollow |
| Node anthocyanin | Absent |
| Color | Yellow |
| Leaf | |
| Color of basal sheath of first leaf | Light green |
| Pubescence | Absent |
| Auricle anthocyanin | Absent |
| Auricle pubescence | Present |
| Color | Dark green |
| Flag leaf orientation (at boot stage) | Recurved |
| Flag leaf glaucosity | Wax present |
| Head | |
| Curvature at maturity | Erect |
| Color at maturity | Yellow |
| Length at maturity | Semi-short (75-84 mm) |
| Shape at maturity | Oblong |

TABLE 1-continued

| | |
|---|---|
| Density at maturity | Dense (2.5-3.2 mm) |
| Number of grains per head (average of 100 heads) | 52.5 |
| Color | Yellow |
| Days from emergence to harvest maturity | 148 |
| Spikelet | |
| Anther coloration | Yellow |
| Glume color of the seventh spikelet | White |
| Glume length at maturity | Medium (8 mm) |
| Glume width at maturity | Medium (3.5 mm) |
| Beak length | Semi-short (2 to 5 mm) |
| Awnedness | Awned |
| Awn color | Yellow |
| Days from emergence to full spikelet | 96 |
| Seed | |
| Weight (g per 1,000 seeds) | 35.5 |
| Shape | Ovoid |
| Texture | Soft |
| Color | Amber |
| Germ size | Medium |
| Germ shape | Ovate |
| Germ edges | Pronounced |
| Brush | Short |
| Brush length | 0.5 mm or less |
| Crease depth | Mid-deep to deep (20-35%) |
| Seed phenol reaction | Brown |

Overview of the Variety '10020777765'

Wheat variety '10020777765' is a spring-type wheat plant with semi-short yellow heads and awned spikelets.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '10020777765'.

Objective Description of the Variety '10020777765'

The cultivar description information (Table 2) provides a summary of wheat cultivar '10020777765' plant characteristics. Those of skill in the art will recognize that these are typical values that may vary due to environment and that other values that are substantially equivalent are within the scope of the invention. As used herein, "a wheat plant having the physiological and morphological characteristics of wheat cultivar '10020777765'" is a plant having the characteristics set forth in Table 2 when grown in the same environmental conditions.

TABLE 2

| Characteristic | Value |
|---|---|
| Plant | |
| Vernalization | Spring |
| Coleoptile color | White |
| Coleoptile anthocyanin | Absent |
| Juvenile plant growth habit | Semi-erect |
| Color at boot stage | Light green |
| Height (cm) | 89 |
| Tillering | Sparse (1 to 3) |
| Stem | |
| Waxy bloom | Present |
| Number of nodes at internode | 4 |
| Internode type | Hollow |
| Node anthocyanin | Absent |
| Color | Yellow |

TABLE 2-continued

| | |
|---|---|
| Leaf | |
| Color of basal sheath of first leaf | Light green |
| Pubescence | Absent |
| Auricle anthocyanin | Absent |
| Auricle pubescence | Present |
| Color | Dark green |
| Flag leaf orientation (at boot stage) | Erect |
| Flag leaf glaucosity | Wax present |
| Head | |
| Curvature at maturity | Erect |
| Color at maturity | Yellow |
| Length at maturity | Semi-short (75-84 mm) |
| Shape at maturity | Oblong |
| Density at maturity | Dense (2.5-3.2 mm) |
| Number of grains per head (average of 100 heads) | 49 |
| Color | Yellow |
| Days from emergence to harvest maturity | 147 |
| Spikelet | |
| Anther coloration | Yellow |
| Glume color of the seventh spikelet | White |
| Glume length at maturity | Medium (8 mm) |
| Glume width at maturity | Medium (3.5 mm) |
| Beak length | Semi-short (2 to 5 mm) |
| Awnedness | Awned |
| Awn color | Yellow |
| Days from emergence to full spikelet | 94 |
| Seed | |
| Weight (g per 1,000 seeds) | 37 |
| Shape | Ovoid |
| Texture | Soft |
| Color | Amber |
| Germ size | Medium |
| Germ shape | Ovate |
| Germ edges | Pronounced |
| Brush | Short |
| Brush length | 0.5 mm or less |
| Crease depth | Mid-deep to deep (20-35%) |
| Seed phenol reaction | Brown |

Overview of the Variety '20646295'

Wheat variety '20646295' is a spring-type wheat plant with semi-short yellow heads and awned spikelets.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '20646295'.

Objective Description of the Variety '20646295'

The cultivar description information (Table 3) provides a summary of wheat cultivar '20646295' plant characteristics. Those of skill in the art will recognize that these are typical values that may vary due to environment and that other values that are substantially equivalent are within the scope of the invention. As used herein, "a wheat plant having the physiological and morphological characteristics of wheat cultivar '20646295'" is a plant having the characteristics set forth in Table 3 when grown in the same environmental conditions.

TABLE 3

| Characteristic | Value |
|---|---|
| Plant | |
| Vernalization | Spring |
| Coleoptile color | White |
| Coleoptile anthocyanin | Absent |
| Juvenile plant growth habit | Semi-erect |
| Color at boot stage | Light green |
| Height (cm) | 80 |
| Tillering | Sparse (1 to 3) |
| Stem | |
| Waxy bloom | Absent |
| Number of nodes at internode | 4 |
| Internode type | Hollow |
| Node anthocyanin | Absent |
| Color | Yellow |
| Leaf | |
| Color of basal sheath of first leaf | Light green |
| Pubescence | Absent |
| Auricle anthocyanin | Absent |
| Auricle pubescence | Present |
| Color | Dark green |
| Flag leaf orientation (at boot stage) | Erect |
| Flag leaf glaucosity | Wax absent |
| Head | |
| Curvature at maturity | Curved |
| Color at maturity | Yellow |
| Length at maturity | Semi-short (75-84 mm) |
| Shape at maturity | Oblong |
| Density at maturity | Dense (2.5-3.2 mm) |
| Number of grains per head (average of 100 heads) | 40 |
| Color | Yellow |
| Days from emergence to harvest maturity | 149 |
| Spikelet | |
| Anther coloration | Yellow |
| Glume color of the seventh spikelet | White |
| Glume length at maturity | Medium (8 mm) |
| Glume width at maturity | Medium (3.5 mm) |
| Awnedness | Awned |
| Awn color | Yellow |
| Days from emergence to full spikelet | 97 |
| Seed | |
| Weight (g per 1,000 seeds) | 34 |
| Shape | Oval |
| Texture | Vitreous |
| Color | Amber |
| Germ size | Medium |
| Germ shape | Round |
| Germ edges | Pronounced |
| Brush | Short |
| Brush length | Between 0.5 to 1 mm |
| Crease depth | Mid-deep to deep (20-35%) |
| Seed phenol reaction | Brown |

FURTHER EMBODIMENTS

Additional methods include, but are not limited to, expression vectors introduced into plant tissues using a direct gene transfer method, such as microprojectile-mediated delivery. DNA injection, electroporation, and the like. More preferably, expression vectors are introduced into plant tissues by using either microprojectile-mediated delivery with a biolistic device or by using *Agrobacterium*-mediated transformation. Transformed plants obtained with the protoplasm of the invention are intended to be within the scope of this invention.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Any DNA sequences, whether from a different species or from the same species, which are introduced into the genome using transformation or various breeding methods, are referred to herein collectively as "transgenes." Over the last fifteen to twenty years, several methods for producing transgenic plants have been developed, and the present invention, in particular embodiments, also relates to transformed versions of the claimed line.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

Plant transformation involves the construction of an expression vector that will function in plant cells. Such a vector contains DNA that contains a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed wheat plants using transformation methods as described below to incorporate transgenes into the genetic material of the wheat plant(s).

Expression Vectors for Wheat Transformation: Marker Genes

Expression vectors include at least one genetic marker, operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley, et al., *PNAS,* 80:4803 (1983). Another commonly used selectable marker gene is the hygromycin phosphotransferase gene which confers resistance to the antibiotic hygromycin (Vanden Elzen, et al., *Plant Mol. Biol.,* 5:299 (1985)).

Additional selectable marker genes of bacterial origin that confer resistance to antibiotics include gentamycin acetyl transferase, streptomycin phosphotransferase, aminoglycoside-3'-adenyl transferase, the bleomycin resistance determinant (Hayford, et al., *Plant Physiol.,* 86:1216 (1988); Jones, et al., *Mol. Gen. Genet.,* 210:86 (1987); Svab, et al., *Plant Mol. Biol.,* 14:197 (1990); Hille, et al., *Plant Mol. Biol.,* 7:171 (1986)). Other selectable marker genes confer resistance to herbicides such as glyphosate, glufosinate, or bromoxynil (Comai, et al., *Nature,* 317:741-744 (1985); Gordon-Kamm, et al., *Plant Cell,* 2:603-618 (1990); and Stalker, et al., *Science,* 242:419-423 (1988)).

Selectable marker genes for plant transformation that are not of bacterial origin include, for example, mouse dihydrofolate reductase, plant 5-enolpyruvylshikimate-3-phosphate synthase, and plant acetolactate synthase (Eichholtz, et al., *Somatic Cell Mol. Genet.,* 13:67 (1987); Shah, et al., *Science,* 233:478 (1986); and Charest, et al., *Plant Cell Rep.,* 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include α-glucuronidase (GUS), α-galactosidase, luciferase, chloramphenicol, and acetyltransferase (Jefferson, R. A., *Plant Mol. Biol.,* 5:387 (1987); Teeri, et al., *EMBO J.,* 8:343 (1989); Koncz, et al., *PNAS,* 84:131 (1987); and DeBlock, et al., *EMBO J.,* 3:1681 (1984)).

In vivo methods for visualizing GUS activity that do not require destruction of plant tissues are available (Molecular Probes, Publication 2908, IMAGENE GREEN, pp. 1-4 (1993) and Naleway, et al., *J. Cell Biol.,* 115: 151a (1991)). However, these in vivo methods for visualizing GUS activity have not proven useful for recovery of transformed cells because of low sensitivity, high fluorescent backgrounds, and limitations associated with the use of GUS genes as selectable markers.

More recently, a gene encoding Green Fluorescent Protein (GFP) has been utilized as a marker for gene expression in prokaryotic and eukaryotic cells (Chalfie, et al., *Science,* 263:802 (1994)). GFP and mutants of GFP may be used as screenable markers.

Expression Vectors for Wheat Transformation: Promoters

Genes included in expression vectors must be driven by a nucleotide sequence containing a regulatory element (for example, a promoter). Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters:

An inducible promoter is operably linked to a gene for expression in wheat. Optionally, the inducible promoter is operably linked to a nucleotide sequence encoding a signal sequence which is operably linked to a gene for expression in wheat. With an inducible promoter, the rate of transcription increases in response to an inducing agent.

Any inducible promoter can be used in the instant invention. See Ward, et al., *Plant Mol. Biol.,* 22:361-366 (1993). Exemplary inducible promoters include, but are not limited to, that from the ACEI system which responds to copper (Meft, et al., *PNAS,* 90:4567-4571 (1993)); In2 gene from maize which responds to benzenesulfonamide herbicide safeners (Hershey, et al., *Mol. Gen. Genet.,* 227:229-237 (1991) and Gatz, et al., *Mol. Gen. Genet.,* 243:32-38 (1994)) or Tet repressor from Tn10 (Gatz, et al., *Mol. Gen. Genet.,* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena, et al., *PNAS,* 88:0421 (1991)).

B. Constitutive Promoters:

A constitutive promoter is operably linked to a gene for expression in wheat or the constitutive promoter is operably linked to a nucleotide sequence encoding a signal sequence which is operably linked to a gene for expression in wheat.

Many different constitutive promoters can be utilized in the instant invention. Exemplary constitutive promoters include, but are not limited to, the promoters from plant viruses such as the 35S promoter from CaMV (Odell, et al., *Nature,* 313:810-812 (1985)) and the promoters from such genes as rice actin (McElroy, et al., *Plant Cell,* 2:163-171 (1990)); ubiquitin (Christensen, et al., *Plant Mol. Biol.,* 12:619-632 (1989) and Christensen, et al., *Plant Mol. Biol.,* 18:675-689 (1992)); pEMU (Last, et al., *Theor. Appl. Genet.,* 81:581-588 (1991)); MAS (Velten, et al., *EMBO J.,* 3:2723-2730 (1984)) and maize H3 histone (Lepetit, et al., *Mol. Gen. Genet.,* 231:276-285 (1992) and Atanassova, et al., *Plant J.,* 2 (3): 291-300 (1992)). The ALS promoter, Xba1/Nco1 fragment 5' to the *Brassica napus* ALS3 structural gene (or a nucleotide sequence similarity to said Xba1/Nco1 fragment), represents a particularly useful constitutive promoter. See PCT Application No. WO 96/30530.

C. Tissue-Specific or Tissue-Preferred Promoters:

A tissue-specific promoter is operably linked to a gene for expression in wheat. Optionally, the tissue-specific promoter is operably linked to a nucleotide sequence encoding a signal sequence which is operably linked to a gene for expression in wheat. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., *Science,* 23:476-482 (1983) and Sengupta-Gopalan, et al., *PNAS,* 82:3320-3324 (1985)); a leaf-specific and light-induced promoter such as that from cab or rubisco (Simpson, et al., *EMBO J.,* 4 (11): 2723-2729 (1985) and Timko, et al., *Nature,* 318:579-582 (1985)); an anther-specific promoter such as that from LAT52 (Twell, et al., *Mol. Gen. Genet.,* 217:240-245 (1989)); a pollen-specific promoter such as that from Zm13 (Guerrero, et al., *Mol. Gen. Genet.,* 244:161-168 (1993)) or a microspore-preferred promoter such as that from apg (Twell, et al., *Sex. Plant Reprod.,* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., *Plant Mol. Biol.,* 20:49 (1992); Close, P. S., Master's Thesis, Iowa State University (1993); Knox, C., et al., "Structure and Organization of Two Divergent Alpha-Amylase Genes from Barley," *Plant Mol. Biol.,* 9:3-17 (1987); Lerner, et al., *Plant Physiol.,* 91:124-129 (1989); Fontes, et al., *Plant Cell,* 3:483-496 (1991); Matsuoka, et al., *PNAS,* 88:834 (1991); Gould, et al., *J. Cell. Biol.,* 108:1657 (1989); Creissen, et al., *Plant J.,* 2:129 (1991); Kalderon, et al., A short amino acid sequence able to specify nuclear location, *Cell,* 39:499-509 (1984); and Steifel, et al., Expression of a maize cell wall hydroxyproline-rich glycoprotein gene in early leaf and root vascular differentiation, *Plant Cell,* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.,* 114:92-6 (1981).

According to a preferred embodiment, the transgenic plant provided for commercial production of foreign protein is wheat. In another preferred embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see *Methods in Plant Molecular Biology and Biotechnology*, Glick and Thompson Eds., 269:284, CRC Press, Boca Raton (1993).

Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

A. Genes That Confer Resistance to Pests or Disease:

Plant defenses are often activated by specific interaction between the product of a disease resistance gene (R) in the plant and the product of a corresponding avirulence (Avr) gene in the pathogen. A plant line can be transformed with one or more cloned resistance gene to engineer plants that are resistant to specific pathogen strains. See, for example Jones et al. (*Science,* 266:7891, 1994) (cloning of the tomato Cf-9 gene for resistance to *Cladosporium fulvum*); Martin et al. (*Science,* 262:1432, 1993) (tomato Pto gene for resistance to *Pseudomonas syringae* pv. tomato); and Mindrinos et al. (*Cell,* 78 (6): 1089-1099, 1994) (*Arabidopsis* RPS2 gene for resistance to *Pseudomonas syringae*).

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. See Beachy et al. (*Ann. Rev. Phytopathol.,* 28:451, 1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody may also be used. See, for example, Tavladoraki et al. (*Nature,* 366:469, 1993), who show that transgenic plants expressing recombinant antibody genes are protected from virus attack. Virus resistance has also been described in, for example, U.S. Pat. Nos. 6,617,496; 6,608,241; 6,015,940; 6,013,864; 5,850,023 and 5,304,730. Additional means of inducing whole-plant resistance to a pathogen include modulation of the systemic acquired resistance (SAR) or pathogenesis related (PR) genes, for example genes homologous to the *Arabidopsis thaliana* NIM1/NPR1/SAI1, and/or by increasing salicylic acid production (Ryals et al., *Plant Cell,* 8:1809-1819, 1996).

Logemann et al. (*Biotechnology,* 10:305, 1992), for example, disclose transgenic plants expressing a barley ribosome-inactivating gene that have an increased resistance to fungal disease. Plant defensins may be used to provide resistance to fungal pathogens (Thomma et al., *Planta,* 216:193-202, 2002). Other examples of fungal disease resistance are provided in U.S. Pat. Nos. 6,653,280; 6,573,361; 6,506,962; 6,316,407; 6,215,048; 5,516,671; 5,773,696; 6,121,436; and 6,316,407.

The use of the herbicide glyphosate for disease control in wheat plants containing event MON89788, which confers glyphosate tolerance, has also been described in U.S. Pat. No. 7,608,761.

B. Genes That Confer Resistance to Insects:

One example of an insect resistance gene includes a *Bacillus thuringiensis* protein, a derivative thereof or a synthetic polypeptide modeled thereon. See, for example, Geiser et al. (*Gene,* 48 (1): 109-118, 1986), who disclose the cloning and nucleotide sequence of a *Bacillus thuringiensis* δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example is a lectin. See, for example, Van Damme et al. (*Plant Molec. Biol.,* 24:25, 1994), who disclose the nucleotide sequences of several *Clivia miniata* mannose-binding lectin genes. A vitamin-binding protein may also be used, such as avidin. See PCT Application No. US93/06487, the contents of which are hereby incorporated by reference. This application teaches the use of avidin and avidin homologues as larvicides against insect pests.

Another insect resistance gene is an enzyme inhibitor, for example, a protease or proteinase inhibitor or an amylase inhibitor. See, for example, Abe et al. (*J. Biol. Chem.,* 262:16793, 1987) (nucleotide sequence of rice cysteine proteinase inhibitor), Huub et al. (*Plant Molec. Biol.,* 21:985, 1993) (nucleotide sequence of cDNA encoding tobacco proteinase inhibitor I), and Sumitani et al. (*Biosci. Biotech. Biochem.,* 57:1243, 1993) (nucleotide sequence of *Streptomyces nitrosporeus* α-amylase inhibitor).

An insect-specific hormone or pheromone may also be used. See, for example, the disclosure by Hammock et al. (*Nature,* 344:458, 1990), of baculovirus expression of cloned juvenile hormone esterase, an inactivator of juvenile hormone; Gade and Goldsworthy (Eds. Physiological System in Insects, Elsevier Academic Press, Burlington, Mass., 2007), describing allostatins and their potential use in pest control; and Palli et al. (*Vitam. Horm.,* 73:59-100, 2005), disclosing use of ecdysteroid and ecdysteroid receptor in agriculture. The diuretic hormone receptor (DHR) was identified in Price et al. (*Insect Mol. Biol.,* 13:469-480, 2004) as a candidate target of insecticides.

Further examples include, without limitation, an insect-specific antibody or an immunotoxin derived therefrom and a developmental-arrestive protein. See Taylor et al. (Seventh Inn Symposium on Molecular Plant-Microbe Interactions, Edinburgh, Scotland, Abstract W97, 1994), who described enzymatic inactivation in transgenic tobacco via production of single-chain antibody fragments. Numerous other examples of insect resistance have been described. Sec, for example, U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658; 5,880,275; 5,763,245 and 5,763,241.

C. Genes that Confer Resistance to a Herbicide:

Numerous herbicide resistance genes are known and may be employed with the invention. An example is a gene conferring resistance to a herbicide that inhibits the growing point or meristem, such as an imidazalinone or a sulfonylurea. Exemplary genes in this category code for mutant ALS and AHAS enzyme as described, for example, by Lee et al., *EMBO J.,* 7:1241, 1988; Gleen et al., *Plant Molec. Biology,* 18:1185-1187, 1992; and Miki et al., *Theor. Appl. Genet.,* 80:449, 1990.

A DNA molecule encoding a mutant aroA gene can be obtained under ATCC Accession Number 39256, and the nucleotide sequence of the mutant gene is disclosed in U.S. Pat. No. 4,769,061 to Comai. A hygromycin B phosphotransferase gene from *E. coli* which confers resistance to glyphosate in tobacco callus and plants is described in Penaloza-Vazquez et al., *Plant Cell Reports,* 14:482-487, 1995. European Patent Application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyltransferase gene is provided in European Patent Application No. 0 242 246 to Leemans et al. DeGree F. et al. (*Biotechnology,* 7:61, 1989), describe the production of transgenic plants that express chimeric bar genes coding for phosphinothricin acetyl transferase activity. Exemplary genes conferring resistance to phenoxy propionic acids and cyclohexanediones, such as sethoxydim and haloxyfop are the Acct-S1, Acct-S2 and Acct-S3 genes described by Marshall et al., (*Theor. Appl. Genet.,* 83:4:35, 1992).

Genes are also known conferring resistance to a herbicide that inhibits photosynthesis, such as a triazine (psbA and gs+ genes) and a benzonitrile (nitrilase gene). Przibila et al. (*Plant Cell,* 3:169, 1991) describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al. (*Biochem. J.,* 285 (Pt 1): 173-180, 1992). Protoporphyrinogen oxidase (PPO) is the target of the PPO-inhibitor class of herbicides; a PPO-inhibitor resistant PPO gene was recently identified in *Amaranthus tuberculatus* (Patzoldt et al., *PNAS,* 103 (33): 12329-2334, 2006). The herbicide methyl viologen inhibits $CO_2$ assimilation. Foyer et al. (*Plant Physiol.,* 109:1047-1057, 1995) describe a plant overexpressing glutathione reductase (GR) which is resistant to methyl viologen treatment.

Siminszky (*Phytochemistry Reviews,* 5:445-458, 2006) describes plant cytochrome P450-mediated detoxification of multiple, chemically unrelated classes of herbicides. Modified bacterial genes have been successfully demonstrated to confer resistance to atrazine, a herbicide that binds to the plastoquinone-binding membrane protein QB in photosystem II to inhibit electron transport. See, for example, studies by Cheung et al. (*PNAS,* 85 (2): 391-395, 1988), describing tobacco plants expressing the chloroplast psbA gene from an atrazine-resistant biotype of *Amaranthus hybridus* fused to the regulatory sequences of a nuclear gene, and Wang et al. (*Plant Biotech. J.,* 3:475-486, 2005), describing transgenic alfalfa, *Arabidopsis,* and tobacco plants expressing the atzA gene from *Pseudomonas* sp. that were able to detoxify atrazine.

Bayley et al. (*Theor. Appl. Genet.,* 83:645-649, 1992) describe the creation of 2,4-D-resistant transgenic tobacco and cotton plants using the 2,4-D monooxygenase gene tfdA from *Alcaligenes eutrophus* plasmid pJP5. U.S. Pat. App. Pub. No. 20030135879 describes the isolation of a gene for dicamba monooxygenase (DMO) from *Pseudomonas maltophilia* that is involved in the conversion of dicamba to a non-toxic 3,6-dichlorosalicylic acid and thus may be used for producing plants tolerant to this herbicide.

Other examples of herbicide resistance, include without limitation those described in U.S. Pat. Nos. 6,803,501; 6,448,476; 6,248,876; 6,225,114; 6,107,549; 5,866,775; 5,804,425; 5,633,435; 5,463,175.

D. Genes That Modify Fatty Acid, Phytate, and Carbohydrate Metabolism:

Genes may be used conferring modified fatty acid metabolism. For example, stearyl-ACP desaturase genes may be used. See Knutzon et al. (*Proc. Natl. Acad. Sci. USA*, 89:2624, 1992). Various fatty acid desaturases have also been described. McDonough et al. describe a *Saccharomyces cerevisiae* OLE1 gene encoding Δ9-fatty acid desaturase, an enzyme which forms the monounsaturated palmitoleic (16:1) and oleic (18:1) fatty acids from palmitoyl (16:0) or stearoyl (18:0) CoA (*J. Biol. Chem.*, 267 (9): 5931-5936, 1992). Fox et al. describe a gene encoding a stearoyl-acyl carrier protein delta-9 desaturase from castor (*Proc. Natl. Acad. Sci. USA*, 90 (6): 2486-2490, 1993). Reddy et al. describe 46- and A12-desaturases from the cyanobacteria *Synechocystis* responsible for the conversion of linoleic acid (18:2) to gamma-linolenic acid (18:3 gamma) (*Plant Mol. Biol.*, 22 (2): 293-300, 1993). A gene from *Arabidopsis thaliana* that encodes an omega-3 desaturase has been identified (Arondel et al. *Science*, 258 (5086): 1353-1355, 1992). Plant 49-desaturases (PCT Application Publ. No. WO 91/13972) and wheat and *Brassica* Δ15-desaturases (European Patent Application Publ. No. EP 0616644) have also been described. U.S. Pat. No. 7,622,632 describes fungal Δ15-desaturases and their use in plants. EP U.S. Pat. No. 1,656,449 describes 46-desaturases from *Primula* as well as wheat plants having an increased stearidonic acid (SDA, 18:4) content. U.S. Pat. App. Pub. No. 2008-0260929 describes expression of transgenic desaturase enzymes in corn plants, and improved fatty acid profiles resulting therefrom.

Modified oil production is disclosed, for example, in U.S. Pat. Nos. 6,444,876; 6,426,447 and 6,380,462. High oil production is disclosed, for example, in U.S. Pat. Nos. 6,495,739; 5,608,149; 6,483,008 and 6,476,295. Modified fatty acid content is disclosed, for example, in U.S. Pat. Nos. 6,828,475; 6,822,141; 6,770,465; 6,706,950; 6,660,849; 6,596,538; 6,589,767; 6,537,750; 6,489,461 and 6,459,018.

Phytate metabolism may also be modified by introduction of a phytase-encoding gene to enhance breakdown of phytate, adding more free phosphate to the transformed plant. For example, see Van Hartingsveldt et al. (*Gene*, 127:87, 1993), for a disclosure of the nucleotide sequence of an *Aspergillus niger* phytase gene. In wheat, this, for example, could be accomplished by cloning and then reintroducing DNA associated with the single allele which is responsible for wheat mutants characterized by low levels of phytic acid. See Raboy et al. (*Plant Physiol.*, 124 (1): 355-368, 2000).

A number of genes are known that may be used to alter carbohydrate metabolism. For example, plants may be transformed with a gene coding for an enzyme that alters the branching pattern of starch. See Shiroza et al. (*J. Bacteriol.*, 170:810, 1988) (nucleotide sequence of *Streptococcus mutans* fructosyltransferase gene), Steinmetz et al. (*Mol. Gen. Genet.*, 20:220, 1985) (nucleotide sequence of *Bacillus subtilis* levansucrase gene), Pen et al. (*Biotechnology*, 10:292, 1992) (production of transgenic plants that express *Bacillus licheniformis* α-amylase), Elliot et al. (*Plant Molec. Biol.*, 21:515, 1993) (nucleotide sequences of tomato invertase genes), Sergaard et al. (*J. Biol. Chem.*, 268:22480, 1993) (site-directed mutagenesis of barley α-amylase gene), and Fisher et al. (*Plant Physiol.*, 102:1045, 1993) (maize endosperm starch branching enzyme II). The Z10 gene encoding a 10 kD zein storage protein from maize may also be used to alter the quantities of 10 kD zein in the cells relative to other components (Kirihara et al., *Gene*, 71 (2): 359-370, 1988).

Genes that may be used to alter antioxidant content or composition, such as alteration of tocopherol or tocotrienols, are also known in the art. For example, manipulation of antioxidant levels through alteration of a phytyl prenyl transferase (ppt) is known, as is manipulation of antioxidant levels through alteration of a homogentisate geranyl geranyl transferase (hggt). Genes that control the content of high-molecular weight gluten subunits (HMW-GS) are also known. Genomic clones have been isolated for different subunits. For example, genomic clones have transformed wheat with genes that encode a modified HMW-GS.

Methods to control amino acid levels and protein and ion metabolism are known. Increased protein metabolism, zinc and iron content, for example, by regulating the NAC gene, increasing protein metabolism by regulating the Gpc-B 1 gene, or regulating glutenin and gliadin genes. Methods of increasing accumulation of essential amino acids in seeds, binary methods of increasing accumulation of essential amino acids in seeds, alteration of amino acid compositions in seeds, methods for altering amino acid content of proteins, alteration of amino acid compositions in seeds, and proteins with enhanced levels of essential amino acids are all known in the art. Other examples may include high, increased, or altered levels of methionine, lysine, threonine, plant amino acid biosynthetic enzymes, plant tryptophan synthase beta subunit, methionine metabolic enzymes, sulfur, sulfur amino acid content, Ces A: cellulose synthase, hemicellulose, UDPGdH, and RGP; or engineered seed protein having higher percentage of essential amino acids, and increasing synthetic storage proteins with defined structure containing programmable levels of essential amino acids for improvement of the nutritional value of plants.

E. Genes Encoding Additional Traits:

Additional traits can be introduced into the wheat variety of the present invention. A non-limiting example of such a trait is a coding sequence which decreases RNA and/or protein levels. The decreased RNA and/or protein levels may be achieved through RNAi methods, such as those described in U.S. Pat. No. 6,506,559 to Fire and Mellow.

Another trait that may find use with the wheat varieties of the invention is a sequence which allows for site-specific recombination. Examples of such sequences include the FRT sequence, used with the FLP recombinase (Zhu and Sadowski, *J. Biol. Chem.*, 270:23044-23054, 1995); and the LOX sequence, used with CRE recombinase (Sauer, *Mol. Cell. Biol.*, 7:2087-2096, 1987). The recombinase genes can be encoded at any location within the genome of the wheat plant, and are active in the hemizygous state.

It may also be desirable to make wheat plants more tolerant to or more easily transformed with *Agrobacterium tumefaciens*. Expression of p53 and iap, two baculovirus cell-death suppressor genes, inhibited tissue necrosis and DNA cleavage. Additional targets can include plant-encoded proteins that interact with the *Agrobacterium* Vir genes; enzymes involved in plant cell wall formation; and histones, histone acetyltransferases and histone deacetylases (reviewed in Gelvin, *Microbiology & Mol. Biol. Reviews*, 67:16-37, 2003).

In addition to the modification of oil, fatty acid or phytate content described above, it may additionally be beneficial to modify the amounts or levels of other compounds. For example, the amount or composition of antioxidants can be altered. See, for example, U.S. Pat. No. 6,787,618; U.S. Pat. App. Pub. No. 20040034886 and International Patent App.

Pub. No. WO 00/68393, which disclose the manipulation of antioxidant levels, and International Patent App. Pub. No. WO 03/082899, which discloses the manipulation of an antioxidant biosynthetic pathway.

Additionally, seed amino acid content may be manipulated. U.S. Pat. No. 5,850,016 and International Patent App. Pub. No. WO 99/40209 disclose the alteration of the amino acid compositions of seeds. U.S. Pat. Nos. 6,080,913 and 6,127,600 disclose methods of increasing accumulation of essential amino acids in seeds.

U.S. Pat. No. 5,559,223 describes synthetic storage proteins in which the levels of essential amino acids can be manipulated. International Patent App. Pub. No. WO 99/29882 discloses methods for altering amino acid content of proteins. International Patent App. Pub. No. WO 98/20133 describes proteins with enhanced levels of essential amino acids. International Patent App. Pub. No. WO 98/56935 and U.S. Pat. Nos. 6,346,403, 6,441,274 and 6,664,445 disclose plant amino acid biosynthetic enzymes. International Patent App. Pub. No. WO 98/45458 describes synthetic seed proteins having a higher percentage of essential amino acids than wild-type.

U.S. Pat. No. 5,633,436 discloses plants including a higher content of sulfur-containing amino acids; U.S. Pat. No. 5,885,801 discloses plants including a high threonine content; U.S. Pat. Nos. 5,885,802 and 5,912,414 disclose plants including a high methionine content; U.S. Pat. No. 5,990,389 discloses plants including a high lysine content; U.S. Pat. No. 6,459,019 discloses plants including an increased lysine and threonine content; International Patent App. Pub. No. WO 98/42831 discloses plants including a high lysine content; International Patent App. Pub. No. WO 96/01905 discloses plants including a high threonine content and International Patent App. Pub. No. WO 95/15392 discloses plants including a high lysine content.

F. Genes that Control Male-Sterility:

Genetic male sterility is available in wheats and, although not required for crossing wheat plants, can increase the efficiency with which hybrids are made, in that it can eliminate the need to physically emasculate the wheat plant used as a female in a given cross. (Brim and Stuber, *Crop Sci.*, 13:528-530, 1973). Herbicide-inducible male sterility systems have also been described. (U.S. Pat. No. 6,762,344).

Where one desires to employ male-sterility systems, it may be beneficial to also utilize one or more male-fertility restorer genes. For example, where cytoplasmic male sterility (CMS) is used, hybrid seed production requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the wheat plant is utilized, but in many cases the seeds will be deemed the most valuable portion of the crop, so fertility of the hybrids in these crops must be restored. Therefore, one aspect of the present invention is directed to plants of the wheat variety '10020777675', '10020777765', or '20646295' including a genetic locus capable of restoring male fertility in an otherwise male-sterile plant. Examples of male-sterility genes and corresponding restorers which could be employed with the plants of the invention are well known to those of skill in the art of plant breeding (see, e.g., U.S. Pat. Nos. 5,530,191 and 5,684,242).

Methods for Wheat Transformation

Numerous methods for plant transformation have been developed, including biological and physical, plant transformation protocols. See, for example, Miki, et al., "Procedures for Introducing Foreign DNA into Plants" in *Methods in Plant Molecular Biology and Biotechnology*, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology*, Glick and Thompson Eds., CRC Press, Inc., Boca Raton, pp. 89-119 (1993).

A. *Agrobacterium*-Mediated Transformation:

One method for introducing an expression vector into plants is based on the natural transformation system of *Agrobacterium*. See, for example, Horsch, et al., *Science*, 227:1229 (1985); Curtis, et al., *Journal of Experimental Botany*, 45:279, 1441-1449 (1994); Torres, et al., *Plant Cell Tissue and Organ Culture*, 34:3, 279-285 (1993); and Dinant, et al., *Molecular Breeding*, 3:1, 75-86 (1997). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Rep.*, 8:238 (1989). See also, U.S. Pat. No. 5,591,616 issued Jan. 7, 1997.

B. Direct Gene Transfer:

Several methods of plant transformation collectively referred to as direct gene transfer have been developed as an alternative to *Agrobacterium*-mediated transformation. A generally applicable method of plant transformation is microprojectile-mediated transformation where DNA is carried on the surface of microprojectiles measuring 1 μm to 4 μm. The expression vector is introduced into plant tissues with a biolistic device that accelerates the microprojectiles to speeds of 300 m/s to 600 m/s which is sufficient to penetrate plant cell walls and membranes. See Russell, D. R., et al., *Plant Cell Rep.*, 12 (3, January), 165-169 (1993); Aragao, F. J. L., et al., *Plant Mol. Biol.*, 20 (2, October), 357-359 (1992); Aragao, F. J. L., et al., *Plant Cell Rep.*, 12 (9, July), 483-490 (1993); Aragao, *Theor. Appl. Genet.*, 93:142-150 (1996); Kim, J., Minamikawa, T., *Plant Sci.*, 117:131-138 (1996); Sanford, et al., *Part. Sci. Technol.*, 5:27 (1987); Sanford, J. C., *Trends Biotech.*, 6:299 (1988); Klein, et al., *Bio/technology*, 6:559-563 (1988); Sanford, J. C., *Physiol. Plant*, 7:206 (1990); Klein, et al., *Bio/technology*, 10:268 (1992).

Another method for physical delivery of DNA to plants is sonication of target cells. Zhang, et al., *Bio/technology*, 9:996 (1991). Alternatively, liposome and spheroplast fusion have been used to introduce expression vectors into plants. Deshayes, et al., *EMBO J.*, 4:2731 (1985) and Christou, et al., *PNAS*, 84:3962 (1987). Direct uptake of DNA into protoplasts using $CaCl_2$) precipitation, polyvinyl alcohol, or poly-L-ornithine has also been reported. Hain, et al., *Mol.*

*Gen. Genet.*, 199:161 (1985) and Draper, et al., *Plant Cell Physiol.*, 23:451 (1982). Electroporation of protoplasts and whole cells and tissues have also been described. See Saker, M., Kuhne, T., Biologia *Plantarum*, 40 (4): 507-514 (1997/98); Donn, et al., In Abstracts of VIIth International Congress on Plant Cell and Tissue Culture IAPTC, A2-38, p. 53 (1990); D'Halluin, et al., *Plant Cell*, 4:1495-1505 (1992); and Spencer, et al., *Plant Mol. Biol.*, 24:51-61 (1994). See also Chupean, et al., *Bio/technology*, 7:5, 503-508 (1989).

Following transformation of wheat target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed with another (non-transformed or transformed) line in order to produce a new transgenic wheat line. Alternatively, a genetic trait which has been engineered into a particular wheat variety using the foregoing transformation techniques could be introduced into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Gene Conversions

When the term "wheat plant" is used in the context of the present invention, this also includes any gene conversions of that variety. The term "gene converted plant" as used herein refers to those wheat plants which are developed by backcrossing, genetic engineering, or mutation, where essentially all of the desired morphological and physiological characteristics of a variety are recovered in addition to the one or more genes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental wheat plant which contributes the gene for the desired characteristic is termed the "nonrecurrent" or "donor parent." This terminology refers to the fact that the nonrecurrent parent is used one time in the backcross protocol and therefore does not recur. The parental wheat plant to which the gene or genes from the nonrecurrent parent are transferred is known as the recurrent parent as it is used for several rounds in the backcrossing protocol. Pochlman & Sleper (1994) and Fehr (1993). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a wheat plant is obtained where essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent variety is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred.

Many gene traits have been identified that are not regularly selected in the development of a new line but that can be improved by backcrossing techniques. Gene traits may or may not be transgenic. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these gene traits are described in U.S. Pat. Nos. 5,777,196, 5,948, 957, and 5,969,212, the disclosures of which are specifically hereby incorporated by reference.

Tissue Culture

Further reproduction of the variety can occur by tissue culture and regeneration. Tissue culture of various tissues of wheat and regeneration of plants therefrom is well known and widely published. For example, reference may be had to Teng, et al., *HortScience*, 27:9, 1030-1032 (1992); Teng, et al., *HortScience*, 28:6, 669-1671 (1993); Zhang, et al., *Journal of Genetics and Breeding*, 46:3, 287-290 (1992); Webb, et al., *Plant Cell Tissue and Organ Culture*, 38:1, 77-79 (1994); Curtis, et al., *Journal of Experimental Botany*, 45:279, 1441-1449 (1994); Nagata, et al., *Journal for the American Society for Horticultural Science*, 125:6, 669-672 (2000); and Ibrahim, et al., *Plant Cell Tissue and Organ Culture*, 28 (2), 139-145 (1992). It is clear from the literature that the state of the art is such that these methods of obtaining plants are routinely used and have a very high rate of success. Thus, another aspect of this invention is to provide cells which upon growth and differentiation produce wheat plants having the physiological and morphological characteristics of variety '10020777675', '10020777765', or '20646295'.

As used herein, the term "tissue culture" indicates a composition containing isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, heads, shoots, glumes, awns, pericarps, endosperms, spikes, anthers, pistils, flowers, seeds, petioles, and the like. Means for preparing and maintaining plant tissue culture are well known in the art. By way of example, a tissue culture containing organs has been used to produce regenerated plants. U.S. Pat. Nos. 5,959,185, 5,973,234, and 5,977,445 describe certain techniques, the disclosures of which are incorporated herein by reference.

Additional Breeding Methods

The invention is also directed to methods for producing a wheat plant by crossing a first parent wheat plant with a second parent wheat plant where the first or second parent wheat plant is a wheat plant of variety '10020777675', '10020777765', or '20646295'. Further, both first and second parent wheat plants can come from wheat variety "10020777675', '10020777765', or '20646295'. Thus, any such methods using wheat variety '10020777675', '10020777765', or '20646295' are part of the invention: selfing, backcrosses, hybrid production, crosses to populations, and the like. All plants produced using wheat variety '10020777675', '10020777765', or '20646295' as at least one parent are within the scope of this invention, including those developed from varieties derived from wheat variety '10020777675', '10020777765', or '20646295'. Advantageously, this wheat variety could be used in crosses with other, different, wheat plants to produce the first generation (F1) wheat hybrid seeds and plants with superior characteristics. The varieties of the invention can also be used for transformation where exogenous genes are introduced and expressed by the varieties of the invention. Genetic variants created either through traditional breeding methods using wheat variety '10020777675', '10020777765', or '20646295', or through transformation of variety '10020777675', '10020777765', or '20646295' by any of a number of protocols known to those of skill in the art are intended to be within the scope of this invention.

The following describes breeding methods that may be used with wheat variety '10020777675', '10020777765', or '20646295' in the development of further wheat plants. One such embodiment is a method for developing variety "10020777675', '10020777765', or '20646295' progeny wheat plants in a wheat plant breeding program, by: obtaining the wheat plant, or a part thereof, of variety '10020777675', '10020777765', or '20646295', utilizing said plant or plant part as a source of breeding material, and selecting a wheat '10020777675', '10020777765', or '20646295' progeny plant with molecular markers in common with variety '10020777675', '10020777765', or '20646295' and/or with morphological and/or physiological characteristics selected from the characteristics listed in the section entitled "Objective description of the variety '10020777675'", "Objective description of the variety '10020777765'", or "Objective description of the variety '20646295'". Breeding steps that may be used in the wheat plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of wheat variety '10020777675', '10020777765', or '20646295' progeny wheat plants, by crossing variety '10020777675', '10020777765', or '20646295' with another wheat plant, thereby producing a population of wheat plants, which, on average, derive 50% of their alleles from wheat variety '10020777675', '10020777765', or '20646295'. A plant of this population may be selected and repeatedly selfed or sibbed with a wheat variety resulting from these successive filial generations. One embodiment of this invention is the wheat variety produced by this method and that has obtained at least 50% of its alleles from wheat variety '10020777675', '10020777765', or '20646295'. One of ordinary skill in the art of plant breeding would know how to evaluate the traits of two plant varieties to determine if there is no significant difference between the two traits expressed by those varieties. For example, see Fehr and Walt, *Principles of Variety Development*, pp. 261-286 (1987). Thus, the invention includes wheat variety '10020777675', '10020777765', or '20646295' progeny wheat plants containing a combination of at least two variety '10020777675', '10020777765', or '20646295' traits selected from those listed in the section entitled "Objective description of the variety '10020777675'", "Objective description of the variety '10020777765'", or "Objective description of the variety '20646295'" so that said progeny wheat plant is not significantly different for said traits than wheat variety '10020777675', '10020777765', or '20646295' as determined at the 5% significance level when grown in the same environmental conditions. Using techniques described herein, molecular markers may be used to identify said progeny plant as a wheat variety '10020777675', '10020777765', or '20646295' progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of wheat variety '10020777675', '10020777765', or '20646295' may also be characterized through their filial relationship with wheat variety '10020777675', '10020777765', or '20646295', as for example, being within a certain number of breeding crosses of wheat variety '10020777675', '10020777765', or '20646295'. A breeding cross is a cross made to introduce new genetics into the progeny, and is distinguished from a cross, such as a self or a sib cross, made to select among existing genetic alleles. The lower the number of breeding crosses in the pedigree, the closer the relationship between wheat variety '10020777675', '10020777765', or '20646295' and its progeny. For example, progeny produced by the methods described herein may be within 1, 2, 3, 4, or 5 breeding crosses of wheat variety '10020777675', '10020777765', or '20646295'.

As used herein, the term "plant" includes plant cells, plant protoplasts, plant cell tissue cultures from which wheat plants can be regenerated, plant calli, plant clumps, and plant cells that are intact in plants or parts of plants, such as leaves, pollen, embryos, cotyledons, hypocotyl, roots, root tips, heads, shoots, glumes, awns, pericarps, endosperms, spikes, anthers, pistils, flowers, ovules, seeds, stems, and the like.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

Wheat Variety '10020777675'

A deposit of at least 625 seeds of the wheat variety '10020777675' was made with the American Type Culture Collection (ATCC), ATCC Patent Depository, 10801 University Boulevard, Manassas, Virginia, 20110, USA, and assigned ATCC number PTA-127799. The seeds deposited with the ATCC Patent Depository on Jul. 9, 2024, were obtained from the seed of the variety maintained by GDM Seeds Inc., having an address at 454 E 300N Rd., Gibson City, Illinois, 60936, United States, since prior to the filing date of the application. Access to this deposit will be available during the pendency of this application to persons determined by the Commissioner of Patents and Trademarks to be entitled thereto under 37 C.F.R. § 1.14 and 35 U.S.C. § 122. Upon issuance, the Applicant will make the deposit available to the public consistent with all of the requirements of 37 C.F.R. § 1.801-1.809. This deposit of the wheat variety '10020777675' will be maintained in the ATCC Patent Depository, which is a public depository, for a period of 30 years, or at least 5 years after the most recent request for a sample of the deposit, or for the effective life of the patent, whichever is longer, and will be replaced if it becomes nonviable during that period. Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

What is claimed is:

1. A wheat seed designated as '10020777675', representative sample of the seed having been deposited under ATCC Accession Number PTA-127799.

2. A wheat plant produced by growing the seed of claim 1.

3. A plant part from the plant of claim 2.

4. The plant part of claim 3, wherein said part is a pollen grain, an ovule, a protoplast, a cell, an embryo, a cotyledon, a hypocotyl, a meristem, a root, a head, a shoot, a glume, an awn, a pericarp, an endosperm, a stem, a spike, a pistil, an anther, a flower, a stem, a leaf, a petiole, or a portion thereof.

5. A wheat plant having all the physiological and morphological characteristics of the wheat plant of claim 2.

6. A plant part from the plant of claim 5.

7. The plant part of claim 6, wherein said part is a pollen grain, an ovule, a protoplast, a cell, an embryo, a cotyledon, a hypocotyl, a meristem, a root, a head, a shoot, a glume, an awn, a pericarp, an endosperm, a stem, a spike, a pistil, an anther, a flower, a stem, a leaf, a petiole, or a portion thereof.

8. An F1 hybrid wheat plant having '10020777675' as a parent where '10020777675' is grown from the seed of claim 1.

9. A pollen grain or an ovule of the plant of claim 2.

10. A tissue culture of the plant of claim 2.

11. A wheat plant regenerated from the tissue culture of claim 10, wherein the plant has all of the morphological and physiological characteristics of a wheat plant produced by growing seed designated as '10020777675' having ATCC Accession Number PTA-127799.

12. A method of making wheat seeds, said method comprising crossing the plant of claim 2 with another wheat plant and harvesting seed therefrom.

13. A method of producing a commodity plant product, comprising obtaining the plant of claim 2 or a part thereof and producing said commodity plant product therefrom.

14. The method of claim 13, wherein the commodity plant product is grain, flour, whole-wheat flour, meal, protein concentrate, baked goods, cereals, pasta, beverages, livestock feed, oil, hulls, biofuel, straw, starches, or construction materials.

15. A method of making a wheat variety designated '10020777675', said method comprising selecting seeds from the cross of one '10020777675' plant with another '10020777675' plant, a sample of '10020777675' wheat seed having been deposited under ATCC Accession Number PTA-127799.

* * * * *